US005837752A

United States Patent [19]
Shastri et al.

[11] Patent Number: 5,837,752
[45] Date of Patent: Nov. 17, 1998

[54] SEMI-INTERPENETRATING POLYMER NETWORKS

[75] Inventors: Venkatram R. Shastri, Allston; Robert S. Langer, Newton, both of Mass.; Peter J. Tarcha, Lake Villa, Ill.

[73] Assignee: Massachusetts Institute of Technology, Cambridge, Mass.

[21] Appl. No.: 895,762

[22] Filed: Jul. 17, 1997

[51] Int. Cl.⁶ .............................. A61F 2/28; C08F 283/00; C08F 283/02
[52] U.S. Cl. .............................. 523/116; 523/115; 525/59; 525/404; 525/411; 525/412; 525/445; 525/450; 525/903; 525/142; 424/423; 424/426; 606/76; 606/77; 623/16
[58] Field of Search .................................... 523/115, 116; 525/59, 404, 411, 412, 445, 450, 903; 522/142; 424/423, 426; 606/76, 77; 623/16

[56] References Cited

U.S. PATENT DOCUMENTS

| | | |
|---|---|---|
| 4,888,413 | 12/1989 | Domb . |
| 5,591,786 | 1/1997 | Oxman ..................................... 525/412 |
| 5,696,178 | 12/1997 | Cooper ..................................... 525/412 |

FOREIGN PATENT DOCUMENTS

WO 93/17669 9/1993 WIPO .

OTHER PUBLICATIONS

Allcock, et al., "Synthesis of poly[(amino acid alkyl ester) phosphazenes]", *Macromolecules* 10(4):824–830 (1977).
Allcock, et al. "Hydrolysis pathways for aminophosphazenes", *Inorg. Chem.* 21(2):515–521 (1982).
Anseth, et al., "Photo–Polymerization of Novel Degradable Networks for Orthopedic Applications", *ACS:PMSE* 74:385–386 (1996).
Coombes, et al., "Gel Casting of Resorbable Polymers: Processing and Applications", *Biomaterials* 13(4):217–224 (1992).
Domb, et al., "Polyanhydrides. I. Preparation of High Molecular Weight Polyanhydrides," *J. Polymer Sci.* 25(12):3373–3386 (1987).
Eggli, et al., "Porous hydroxyapatite and tricalcium phosphate cylinders with two different pore size ranges implanted in the cancerous bone of rabbits", *Clin. Orthop.* 232:127–138 (1987).
Elgendy, et al., "Osteoblast–like cell (MC3T3–E1) proliferation on bioerodible polymers: An approach towards the development of a bone–bioerodible polymer composite material", *Biomaterials* 14(4):263–269 (1993).
Frame, "Hydroxyapatite as a biomaterial for alveolar ridge augmentation", *Int. J. Oral Maxillofacial Surgery* 16(6):642–655 (1987).

Friedlaender, "Current Review: Bone Grafts", *J. Bone and Joint Surgery* 69A(5):786–790 (1987).
Gilding, et al., "Biodegradable polymers for use in surgery: Polyglycolic acid/polylactic acid homo– and copolymers", *Polymer* 20:1459–1464 (1979).
Goethals, Ed., *Polymeric Amines and Ammonium Salts* (Pergamen Press, Elmsford, NY 1980) (Table of Contents).
Hill, et al., "Studies of Polymerization and Ring Formation, XIV. A Linear Superpolyanhyudride and Cyclic Dimeric Anhydride from Sebacic Acid," *J.A.C.S.* 54:1569–1579 (1932).
Hollinger, "Preliminary report on the osteogenic potential of a biodegradable copolymer of polyactide (PLA) and polyglycoide (PGA)" *J. Biomed. Mater. Res.* 17(1):71–82 (1983).
Hollinger, et al., "Biodegradable bone repair materials: Synthetic polymers and ceramics", *Clin. Orthop.* 207:290–305 (1986).
Klaitwatter, et al., "Application of porous ceramics for the attachment of load bearing orthopedic applications", *J. Biomed. Mater. Res. Symp.* 2:161–229 (1971).
Kulkarni, et al., "Biodegradable Poly(lactic acid) Polymers," *J. Biomed. Mater. Res.* 5:169–181 (1971).
March, *Advanced Organic Chemistry* (4th ed., Wiley–Interscience Publication, NY 1992) (Table of Contents).
Parsons, et al., "Osteoconductive Composite Grouts for Orthopedic Use", *Annals N.Y. Academy of Sciences* 523:190–207 (1988).
Potin, et al., "Polyphosphazenes: Synthesis, structures, properties, applications", *Eur. Polym. J.* 27(4/5):341–348 (1991).
Rosen, et al., "Bioerodible polyanhydries for controlled drug delivery," *Biomaterials* 4:131–132 (1983).
White, et al., "Biomaterial aspects of Interpore 200 porous hydroxyapatite", *Dental Clinical of N. Amer.* 30:49–67 (1986).

*Primary Examiner*—David Buttner
*Attorney, Agent, or Firm*—Arnall Golden & Gregory, LLP

[57] ABSTRACT

Compositions for bone repair have been developed based on linear hydrophobic degradable polymers and monomers or macromers, at least one of which includes an anhydride linkage. The monomers and/or macromers crosslink each other but not to the linear polymer to form semi-interpenetrating networks. The compositions can include various excipients, therapeutic and/or diagnostic agents. The compositions can be polymerized in the presence of dissolvable particles such as inorganic salts and proteinaceous materials to provide a porous polymer network. The compositions can be injected into a patient and polymerized in situ or can be polymerized ex vivo and implanted. When polymerized ex vivo, the composition can be shaped into various articles, such as pins, screws, and hollow tubes, which can be used to repair broken bones.

32 Claims, No Drawings

SEMI-INTERPENETRATING POLYMER NETWORKS

BACKGROUND OF THE INVENTION

The present invention is generally in the area of using polymeric semi-interpenetrating polymer network compositions in medical treatments, especially bone repairs.

Successful design of an implant to replace skeletal tissue requires knowledge of the structure and mechanical properties of bone and an understanding of the means by which grafts become incorporated into the body. This information can then be used to define desirable characteristics of the implant to ensure that the graft functions in a manner comparable to organic tissue.

A graft may be necessary when bone fails and does not repair itself in the normal amount of time or when bone loss occurs through injury or cancer. Bone grafts must serve a dual function: to provide mechanical stability and to be a matrix or environment for osteogenesis. Since skeletal injuries are repaired by the regeneration of bone rather than by the formation of scar tissue, grafting is a viable means of promoting healing of osseous defects, as reviewed by Friedlaender, G. E., "Current Concepts Review: Bone Grafts," *Journal of Bone and Joint Surgery*, 69A(5), 786–790 (1987). Osteoinduction and osteoconduction are two mechanisms by which a graft may stimulate the growth of new bone. In the former case, inductive signals of little-understood nature lead to the phenotypic conversion of connective tissue cells to bone cells. In the latter, the implant provides a scaffold for bony ingrowth.

The bone remodeling cycle is a continuous event involving the resorption of pre-existing bone by osteoclasts and the formation of new bone by the work of osteoblasts. Normally, these two phases are synchronous and bone mass remains constant. However, the processes become uncoupled when bone defects heal and grafts are incorporated. Osteoclasts resorb the graft, a process which may take months. More porous grafts revascularize more quickly and graft resorption is more complete. Bone formation begins after the graft has been resorbed. Bone mass and mechanical strength return to near normal.

Present methods for the repair of bony defects include grafts of organic and synthetic construction. Three types of organic grafts are commonly used: autografts, allografts, and xenografts. An autograft is tissue transplanted from one site to another in the patient. The benefits of using the patient's tissue are that the graft will not evoke a strong immune response and that the material is vascularized, which allows for speedy incorporation. However, using an autograft requires a second surgery, which increases the risk of infection and introduces additional weakness at the harvest site. Further, bone available for grafting can only be removed from a limited number of sites, for example, the fibula, ribs and iliac crest. An allograft is tissue taken from a different individual of the same species, and a xenograft from an individual of a different species. The latter types of tissue are readily available in larger quantities than autografts, but genetic differences between the donor and recipient may lead to rejection of the graft.

Synthetic implants may obviate many of the problems associated with organic grafts. Further, synthetics can be produced in a variety of stock shapes and sizes, enabling the surgeon to select implants as his needs dictate, as described by Coombes, A. D. A. and J. D. Heckman, "Gel Casting of Resorbable Polymers: Processing and Applications," *Biomaterials*, 13(4):217–224 (1992). Metals, calcium phosphate ceramics and polymers have all been used in grafting applications.

Calcium phosphate ceramics are used as implants in the repair of bone defects because these materials are non-toxic, non-immunogenic, and are composed of calcium and phosphate ions, the main constituents of bone (Jarcho, 1981; Frame, J. W., "Hydroxyapatite as a biomaterial for alveolar ridge augmentation," *Int. J. Oral Maxillofacial Surgery*, 16, 642–55 (1987); Parsons, et al. "Osteoconductive Composite Grouts for Orthopedic Use," *Annals N.Y. Academy of Sciences*, 523, 190–207 (1988)). Both tricalcium phosphate (TCP) $[Ca_3(PO_4)_2]$ and hydroxyapatite (HA) $[Ca_{10}(PO_4)_6(OH_2)]$ have been widely used. However, the mechanical properties of calcium phosphate ceramics make them ill-suited to serve as a structural element. Ceramics are brittle and have low resistance to impact loading.

There has been a tremendous increase in applications for polymeric materials over the last decade. They have been used widely in surgical implants, and artificial organs, as reviewed by D. K. Gilding and A. M. Reed, "Biodegradable polymers for use in surgery: Polyglycolic acid/polylactic acid homo- and copolymers," *Polymer* 20, 1459–1464 (1979); J. O. Hollinger and G. C. Battisone, "Biodegradable bone repair materials: Synthetic polymers and ceramics," *Clin. Orthop.*, 207, 290–305 (1986); J. O. Hollinger, "Preliminary report on the osteogenic potential of a biodegradable copolymer of polylactide (PLA) and polyglycolide (PGA)." *J. Biomed. Mater. Res.* 17, 71–82 (1983); and P. Potin and R. De Jaeger, "Polyphosphazenes: Synthesis, structures, properties, applications," *Eur. Polym. J.*, 27, 341–348 (1991). These materials are well suited to implantation as they can serve as a temporary scaffold to be replaced by host tissue, degrading by hydrolysis to non-toxic products, which are excreted, as described by Kulkarni, et al., *J. Biomedical Materials Research*, 5, 169–81 (1971); Hollinger, J. O. and G. C. Battistone, "Biodegradable Bone Repair Materials," *Clinical Orthopedics and Related Research*, 207, 290–305 (1986). Four polymers widely used in medical applications are poly(paradioxanone) (PDS), poly(lactic acid) (PLA), poly(glycolic acid) (PGA), and PLGA copolymers. Copolymerization enables modulation of the degradation time of the material. By changing the ratios of crystalline to amorphous polymers during polymerization, properties of the resulting material can be altered to suit the needs of the application.

These polymers, including poly(lactide-co-glycolic) acid (PLGA), have been used as polymer composites for bone replacement as reported by H. M. Elgendy, et al. "Osteoblast-like cell (MC3T3-E1) proliferation on bioerodible polymers: An approach towards the development of a bone-bioerodible polymer composite material," *Biomaterials*, 14, 263–269 (1993). A limitation of these materials is that they cannot be polymerized in situ to cement broken bones together.

Cyanoacrylate materials have been used as bone cements because they are capable of polymerizing in situ. However, while they provide reasonably strong adhesion, they have proven to be brittle. Conventional bone cement, polymethyl methacrylate (PMMA) is applied in the operating room by mixing powdered polymerized methylmethacrylate in combination with a small amount of benzoyl peroxide and liquid methylmethacrylate monomer. Since the monomer is a reactive molecule and tends to polymerize with itself slowly over time, hydroquinone is added to inhibit spontaneous free radical polymerization. Dimethyl toluidine (DMT) is also included to reduce the threshold temperature for the formation of free radicals by the benzoyl peroxide. When the liquid and powder are mixed by the surgeon, the PMMA powder is partially dissolved by the solvent action of the MMA monomer to form an opaque, viscous liquid. The mixture forms a rock-hard substance within about 10 minutes as a result of free radical polymerization. The original prepolymerized PMMA powder is chemically and mechanically bonded with the surrounding newly formed PMMA.

PMMA is not biodegradable. A biodegradable polymer having controlled biodegradability; significant adherence to the site (either tissue or bone); moldability within an acceptable working time; adequate physical strength; environmental stability; and ability to incorporate sustained release drugs, hormones, growth factors, and other biologically active compounds would be preferable for use as an alternative bone cement and polymer for controlled release.

It is therefore an object of the present invention to provide biodegradable, biocompatible polymeric materials having mechanical and chemical properties suitable for biochemical use as bone cements and tissue implants.

SUMMARY OF THE INVENTION

Compositions useful as bone cements, dental materials, fillers, tissue implants, and as bone grafts, pins, screws, plates, stents, and other articles of manufacture, and methods of preparation and use thereof, are disclosed.

The compositions include at least two components. The first component is a linear polymer, either a linear hydrophobic biodegradable polymer or a linear, non-biodegradable hydrophilic polymer. The second component is one or more crosslinkable monomers or macromers. At least one of the monomers or macromers includes a degradable linkage, preferably an anhydride linkage. When these components are mixed, and the crosslinkable component is crosslinked, a semi-interpenetrating polymer network is formed.

The compositions can optionally include a reactive diluent, which can be used to modify the viscosity of the composition and/or to adjust the cure rate, and non-reactive viscosity modifiers.

The compositions can also include particles of excipients, for example, plaster of paris, hydroxyapatite and other ceramics.

The compositions can also include various therapeutic and/or diagnostic agents. The agents can be incorporated in the composition directly, or can be incorporated in microparticles which are then incorporated into the composition. Incorporating the agents in microparticles can be advantageous for those agents which are reactive with one or more of the components of the composition, i.e, agents which have hydroxy or amine functionality which are incorporated into compositions including anhydride linkages.

The compositions can also include various particles such as inorganic salts and proteinaceous materials which are capable of dissolving under conditions which do not significantly dissolve the composition, which create porosity in the composition once the particles have dissolved. The materials can be selected to have a desired size or size distribution, and can be evenly distributed throughout the composition to provide controlled porosity.

The composition can have a viscosity before crosslinking, ranging from a viscous liquid suitable for injection to a moldable, paste-like putty. The viscosity can be adjusted by adding reactive diluents and/or by adding appropriate solvents.

Suitable solvents are those which are non-reactive with any of the components of the composition. Because an anhydride linkage is present, it is preferable that no protic solvents are used. Halogenated solvents may be used in those embodiments where the composition is polymerized ex vivo, where the solvents can be effectively removed prior to implanting articles of manufacture prepared from the crosslinked composition. For in vivo applications, it is preferred to use solvents which are non-toxic. Suitable solvents for these applications include glyme, dimethylsulfoxide (DMSO) and other polar aprotic solvents.

The compositions can be polymerized ex vivo to provide solid articles, such as pins and screws, which can be used to repair bones. Alternatively, the compositions can be polymerized in situ to function as a bone cement. For those areas which can be accessed via injection, the composition is preferably fluid when applied, and solid when polymerized.

The composition can be polymerized using any suitable free-radical initiators. Examples include photoinitiators and thermally activatable initiators. Preferably, when the crosslinking occurs in vivo, the polymerization conditions are mild enough not to damage surrounding tissue. Polymerization can occur by exposing the composition to an exogenous source of active species, typically electromagnetic radiation, preferably visible or near ultraviolet light. When the compositions are crosslinked, they form semi-interpenetrating polymer networks.

DETAILED DESCRIPTION OF THE INVENTION

Compositions useful as bone cements, tissue implants, dental materials, fillers, and as bone grafts, pins, screws, plates, stents, and other articles of manufacture, and methods of preparation and use thereof, are disclosed.

The compositions include at least two components. The first component is a linear, hydrophobic biodegradable polymer, preferably a homopolymer or copolymer which includes hydroxy acid and/or anhydride linkages or a linear, non-biodegradable hydrophilic polymer, preferably polyethylene oxide or polyethylene glycol. The second component is one or more crosslinkable monomers or macromers. At least one of the monomers or macromers includes a degradable linkage, preferably an anhydride linkage. The linear polymer preferably constituted between 10 and 90% by weight of the composition, more preferably between 30 and 70% of the composition. The crosslinked polymer preferably constitutes between about 30 and 70% by weight of the semi-interpenetrating network composition, more preferably, between 40 and 60 percent of the composition, with the balance being excipients, therapeutic agents, and other components. The compositions form semi-interpenetrating polymer networks when these components are mixed, and the crosslinkable component is crosslinked. Semi-interpenetrating networks are defined as compositions that include two independent components, where one component is a crosslinked polymer and the other component is a non-crosslinked polymer.

The compositions can have a viscosity before crosslinking anywhere between a viscous liquid suitable for injection to a moldable, paste-like putty. The viscosity can be adjusted by adding reactive diluents and/or by adding appropriate solvents. When crosslinked, however, the compositions are solid semi-interpenetrating networks which are capable of supporting bone growth and repair.

Linear, Hydrophobic Biodegradable Polymers

Linear polymers are defined as homopolymers or block copolymers that are not crosslinked. Hydrophobic polymers are well known to those of skill in the art. Biodegradable polymers are those that have a half life under physiological conditions of between about two hours and one year, preferably less than six months, more preferably, less than three months.

Examples of suitable biodegradable polymers include polyanhydrides, polyorthoesters, polyhydroxy acids, polydioxanones, polycarbonates, and polyaminocarbonates. Preferred polymers are polyhydroxy acids and polyanhydrides. Polyanhydrides are the most preferred polymers.

Linear, Hydrophilic Non-Biodegradable Polymers

Linear, hydrophilic polymers are well known to those of skill in the art. Non-biodegradable polymers are those that have a half life longer than approximately one year under physiological conditions. Examples of suitable hydrophilic non-biodegradable polymers include poly(ethylene glycol), poly(ethylene oxide), partially or fully hydrolyzed poly (vinyl alcohol), poly(ethylene oxide)-co-poly(propylene oxide) block copolymers (poloxamers and meroxapols) and poloxamines. Preferred polymers are poly(ethylene glycol), poloxamines, poloxamers and meroxapols. Poly(ethylene glycol) is the most preferred polymer.

Monomers and Macromers

The composition includes one or more monomers or macromers. However, at least one of the monomers or macromers includes an anhydride linkage. Other monomers or macromers that can be used include biocompatible monomers and macromers which include at least one free-radical polymerizable group For example, polymers including ethylenically unsaturated groups which can be photochemically crosslinked may be used, as disclosed in WO 93/17669 by the Board of Regents, University of Texas System, the disclosure of which is incorporated herein by reference.

Suitable polymerizable groups include ethylenically unsaturated groups (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. The preferred polymerizable groups are acrylates, diacrylates, oligoacrylates, dimethacrylates, oligomethacrylates, and other biologically acceptable photopolymerizable groups. (Meth)acrylates are the most preferred active species polymerizable group.

These functional groups can be present on hydrophobic or hydrophilic polymers, which can be used to adjust the hydrophobicity of the compositions. Suitable hydrophobic polymers include those described above. Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

The polymers can be biodegradable, but are preferably of low biodegradability (for predictability of dissolution) but of sufficiently low molecular weight to allow excretion. The maximum molecular weight to allow excretion in human beings (or other species in which use is intended) will vary with polymer type, but will often be about 20,000 daltons or below.

The polymers can include two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

Methods for the synthesis of these polymers are well known to those skilled in the art. See, for example *Concise Encyclopedia of Polymer Science* and *Polymeric Amines and Ammonium Salts,* E. Goethals, editor (Pergamen Press, Elmsford, N.Y. 1980). Many polymers, such as poly(acrylic acid), are commercially available. Naturally occurring and synthetic polymers may be modified using chemical reactions available in the art and described, for example, in March, "Advanced Organic Chemistry," 4th Edition, 1992, Wiley-Interscience Publication, New York.

Preferably, the monomers and/or macromers that include free-radical polymerizable groups include slightly more than one crosslinkable group on average per molecule, more preferably, two or more polymerizable or crosslinkable groups on average per molecule. Because each polymerizable group will polymerize into a chain, crosslinked materials can be produced using only slightly more than one reactive group per polymer (i.e., about 1.02 polymerizable groups on average).

Reactive Diluents

The monomers or macromers are considered reactive diluents if they modify the viscosity of the composition and adjust the cure rate of the composition. Reactive diluents include those monomers and macromers described above.

Excipients

The compositions can also include particles of excipients, for example, ceramics. Specific excipients include hydroxyapatite, plaster of paris, calcium carbonate, tricalcium phosphate, polyphosphates, polyphosphonates and polyphosphites.

Therapeutic Agents

The compositions can also include various therapeutic and/or diagnostic agents. The agents can be incorporated in the composition directly, or can be incorporated in microparticles which are then incorporated into the composition. Incorporating the agents in microparticles can be advantageous for those agents which are reactive with one or more of the components of the composition, i.e, agents which have hydroxy or amine functionality which are incorporated into compositions including anhydride linkages. Microparticles, and methods of preparation thereof, are well known to those of skill in the art.

Examples of therapeutic agents which can be incorporated into the compositions include proteins, polysaccharides, nucleic acid molecules, and synthetic organic or inorganic molecules. These may be useful for therapeutic or diagnostic purposes. Drugs which can be used include anaesthetics, antibiotics, antivirals, nucleic acids, chemotherapeutic agents, anti-angiogenic agents, hormones, drugs having an effect on vascular flow and anti-inflammatories.

The compositions can be combined with humoral factors to promote cell transplantation and engraftment. For example, the compositions can be combined with angiogenic factors, antibiotics, anti-inflammatories, growth factors, compounds which induce differentiation, and other factors which are known to those skilled in the art of cell culture. Nucleic acid molecules include genes, antisense molecules which bind to complementary DNA to inhibit transcription, ribozymes and ribozyme guide sequences. Proteins are defined as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered. Compounds with a wide range of molecular weight, for example, between 50 and 500,000 grams per mole, can be incorporated into the composition.

Diagnostic Agents

Any of a variety of diagnostic agents can be incorporated within the compositions, which can locally or systemically deliver the incorporated agents following administration to a patient. Imaging agents can be used which allow one to monitor bone repair following implantation of the compositions in a patient. Suitable imaging agents include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates currently available, such as diethylene triamine pentaacetic acid (DTPA) and gadopentotate dimeglumine, as well as iron, magnesium, manganese, copper and chromium.

Examples of materials useful for CAT and x-rays include iodine based materials, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

These agents can be detected using standard techniques available in the art and commercially available equipment.

Porosity Forming Agents

The compositions can also include various inorganic salts and/or proteinaceous materials such as gelatin which dissolve at a relatively faster rate under physiological conditions than the composition. The relatively rapid dissolution of these particles creates porosity in the composition once the particles have dissolved. The materials can be selected to have a desired size or size distribution, and can be evenly distributed throughout the composition to provide controlled porosity.

Suitable materials include particles of salts. The particles can be any salt that forms crystals or particles having a diameter of approximately 100 to 250 microns, which is easily removed from and does not react with the polymer, and is non-toxic if some residue remains in the polymer after leaching. Further, the microparticles described above can also be used to provide porosity, if they degrade at a faster rate than the crosslinked composition. Examples of other porosity forming agents include proteins such as gelatin and agarose, starches, polysaccharides such as alginate and other polymers. Preferably, the salt is a sodium salt, such as sodium chloride, sodium tartrate and sodium citrate, and other water soluble salts not soluble in the polymer solvent, for example, THF. The most preferred salt is sodium chloride.

Preferably, the particles are first sieved through a mesh or a series of screens to provide particles of relatively uniform diameter. The particles are then added to the composition. The initial weight fraction of porosity forming agents is preferably between 0.02 and 0.9 dry weight percent. The initial weight fraction is instrumental in determining the characteristics of the semi-interpenetrating polymer matrix.

A particulate leaching process can be used to create a porous polymeric matrix. In one embodiment, salt particles are suspended in a solution including the linear polymer and the reactive monomers or macromers, the solvent is removed, and the particles are leached out of the hardened polymer after the monomers and/or macromers are polymerized. Because anhydride bonds are present in the composition, it is preferable to avoid using aqueous solutions to remove salts to create porosity, but rather, to allow physiological solutions to create the porosity.

Removal of the particles will create a polymer matrix having a plurality of relatively evenly spaced interconnected interstitial spaces or pores, formerly occupied by the particle crystals, into which cells can migrate, attach, and proliferate. The porosity of the matrix can be very high, typically between 60 and 90%, depending on the amount of incorporated particles.

A porous system allows an interconnecting pore network, as described by H. R. Allcock, et al., "Synthesis of poly[(amino acid alkyl ester) phosphazenes]," *Macromolecules*, 10, 824–830 (1977); H. R. Allcock, et al., "Hydrolysis pathways for aminophosphazenes," *Inorg. Chem.*, 21, 515–521 (1982); and Eggli, P. S., et al., "Porous hydroxyapatite and tricalcium phosphate cylinders with two different pore size ranges implanted in the cancerous bone of rabbits", *Clin. Orthop.*, 232, 127–138 (1987); which facilitates the invasion of cells and promotes an organized growth of the incoming cells and tissue. The porosity has been demonstrated to influence the biocompatibility and bony integration on various porous materials by White and Shors, "Biomaterial aspects of Interpore 200 porous hydroxyapatite". *Dental Clinical of N. Amer.*, 30, 49–67 (1986). Klaitwatter, et al., "Application of porous ceramics for the attachment of load bearing orthopedic applications" *J. Biomed. Mater. Res. Symp.*, 2, 161 (1971), have shown that a pore size of over a 100 μm is suitable and necessary for regenerating cells and bony ingrowth.

As described above, the pores in the composition can have a pore size in the range of between approximately 100 and 250 microns, by appropriate selection of the size of the leachable particles.

Solvents

The composition can be dissolved in a solvent that does not adversely affect or react with the components or any particles to be suspended in the solution. The relative amount of solvent will have a minimal effect on the structure of the produced matrix, but will affect the solvent evaporation time. The concentration of the composition in the solvent will typically be in the range of between one and 50 percent, preferably between 10 and 30% w/v.

Solvents should be non-reactive with the components of the composition. It is preferable that no protic solvents are used since anhydride linkages are present. Halogenated solvents may be used in those embodiments where the composition is polymerized ex vivo, where the solvents can be effectively removed prior to implanting articles of manufacture prepared from the crosslinked composition. It is preferred to use solvents which are non-toxic for in vivo applications. Suitable solvents for these applications include glyme, dimethylsulfoxide (DMSO) and other polar aprotic solvents.

Methods of Using the Compositions

The compositions contain free-radical polymerizable groups that, when polymerized, crosslink the compositions to form semi-interpenetrating networks.

The compositions can be polymerized ex vivo to form solid articles for implantation, or can be polymerized in situ and used as a bone cement or, in dental applications, to form artificial teeth or to replace or repair damaged bones, for example, the jawbone.

Ex Vivo Polymerization

When the composition is polymerized ex vivo, the viscosity of the composition is preferably that of a paste or a liquid, such that the material can be molded to a desired shape and the monomers or macromers can be crosslinked. Suitable shapes include screws, pins, stents, hollow tubes, and shunts.

A solution or dispersion of the composition can be cast or injected into any appropriate mold. The resulting semi-interpenetrating polymer network formed after the monomers and/or macromers are polymerized will retain the shape of the mold. The solvent is then evaporated from the composition over a period of time, for example, 24 hours at room temperature. Any residual solvent can be subsequently removed by lyophilization.

In Situ Polymerization

It is preferable for certain applications when the composition is polymerized in situ for the composition to be fluid enough to be injectable. Following injection into a site in a patient, the composition can be crosslinked to form a solid polymer network.

The composition can be used as a bulking agent for hard tissue defects, such as bone or cartilage defects. Examples of this would be in injection into the area surrounding the skull where a bony deformity exists secondary to trauma, or, in the case of complex fractures of long bones, such as the femur or tibia, injection into the bone or area of bone loss or fragmentation. The injection in these instances can be made directly into the needed area with the use of a needle and syringe under local or general anesthesia. In addition, the composition can be used in reconstructive surgery.

For use in dental applications, the viscosity is preferably that of a thick enough paste that can be applied to the surface of a broken tooth such that the composition will maintain a desired shape, and will harden when polymerized. The viscosity can be adjusted by adding appropriate viscosity modifying agents.

Methods of Polymerizing the Composition

The composition can be polymerized using any suitable free-radical initiators (active species), for example, photoinitiators and thermally activatable initiators (in a concentration not toxic to cells, less than 1% by weight, more preferably between 0.05 and 0.01% by weight percent initiator). When the compositions are crosslinked, they form semi-interpenetrating polymer networks.

The teachings of the cited publications are indicative of the level of skill and the general knowledge of those skilled in the art. To the extent necessary, the publications are specifically incorporated herein by reference.

Where appropriate, the following definitions are to be used.

"Electromagnetic Radiation" as used herein refers to energy waves of the electromagnetic spectrum including, but not limited to, x-ray, ultraviolet, visible, infrared, far infrared, microwave and radio-frequency.

"Visible light" as used herein refers to energy waves having a wavelength of at least approximately $4.0 \times 10^{-5}$ cm.

"Ultraviolet light" as used herein refers to energy waves having a wavelength of at least approximately $1.0 \times 10^{-5}$ cm but less than $7.0 \times 10^{-5}$ cm.

"Ultraviolet light" as used herein refers to energy waves having a wavelength of at least approximately $1.0 \times 10^{-5}$ cm but less than $4.0 \times 10^{-5}$ cm.

"Blue light" as used herein refers to energy waves having a wavelength of at least approximately $4.5 \times 10^{-5}$ cm but less than $4.9 \times 10^{-5}$ cm.

"Radiation source" as used herein refers to a source of radiation (as defined above). Examples include, but are not limited to, lamps, the sun, blue lamps, and ultraviolet lamps.

Suitable thermally activatable initiators include various peroxides and azobisisobutyronitrile (AIBN). Suitable photoinitiators include those photoinitiators that are capable of crosslinking the composition upon exposure to light equivalent to between 0.01 mW/cm$^2$ and 1 Watt/cm$^2$. A minimum of 0.01 mW/cm$^2$ intensity is needed to induce polymerization. Maximum light intensity can range from one to 1000 mW/cm$^2$, depending upon the wavelength of radiation. Photoinitiators that generate an active species on exposure to UV light are well known to those of skill in the art.

Tissues can be exposed, to higher light intensities, for example, longer wavelength visible light, which causes less tissue/cell damage than shortwave UV light. In dental applications, blue light (470–490 nm) is used at intensities of 100 to 400 mW/cm$^2$ clinically.

Preferably, when the crosslinking occurs in vivo, the polymerization conditions are mild enough not to damage surrounding tissue. Although discussed herein principally with regard to administration of a light source external to the skin, this should be interpreted as equally applicable to light applied through tissues, for example, from a catheter in a blood vessel adjacent to where the composition has been injected, or in the space adjacent to a bone to be repaired.

The depth of penetration can be controlled by the wavelength of the light used to cause the photopolymerization. For example, visible light penetrates deeper through tissue than UV light. Penetration through tissue can range from microns to one cm, with one cm occurring with visible light. In a preferred embodiment, radiation with a wavelength between 200 and 700 mn is used to create active species and polymerize the network.

The polymerizable groups in the composition can be polymerized using photoinitiators that generate active species upon exposure to UV light, or, preferably, using long-wavelength ultraviolet light (LWUV) or visible light, for example, by photon absorption of certain dyes and chemical compounds. LWUV and visible light are preferred because they cause less damage to tissue and other biological materials than UV light. Useful photoinitiators are those which can be used to initiate polymerization of the macromers without cytotoxicity and within a short time frame, minutes at most and most preferably seconds.

Exposure of dyes and cocatalysts such as amines to visible or LWUV light can generate active species. Light absorption by the dye causes the dye to assume a triplet state, and the triplet state subsequently reacts with the amine to form a active species which initiates polymerization. Polymerization can be initiated by irradiation with light at a wavelength of between about 200–700 nm, most preferably in the long wavelength ultraviolet range or visible range, 320 nm or higher, and most preferably between about 365 and 514 nm.

Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst.

The compositions can be polymerized ex vivo to provide solid articles, such as pins and screws, which can be used to repair bones. Alternatively, the compositions can be polymerized in situ to function as a bone cement. For those areas which can be accessed via injection, the composition is preferably fluid when applied, and solid when polymerized.

Implantation of the Matrix

The matrix described here is implanted using standard surgical techniques for repair or replacement of bone. The matrix can be directly implanted into the site where bone growth is desired. In the preferred embodiment, the matrix will be pre-cast into a desired shape for repair of the bone in need of treatment thereof.

The present invention will be further understood by reference to the following non-limiting examples.

EXAMPLE 1

Synthesis of Photo-Curable Monomers and Polymers

MATERIALS AND METHODS

The mixed methacrylic anhydride of Sebacic acid (SA-Me$_2$) and 1,3-bis (p-carboxy phenoxy) propane (CPP-Me$_2$) were synthesized as described by Anseth et al. (K. S. Anseth, V. R. Shastri, and R. Langer, "Photo-Polymerization of Novel Degradable Networks for Orthopedic Applications", ACS:PMSE, 74, 385, 1996) and characterized by NMR and IR. As shown by Hill and Carothers (Hill and Carothers, "J.A.C.S., 54, 1689, 1932), mixed anhydrides of many aliphatic carboxylic diacids cannot be prepared as pure monomeric entities, due to spontaneous cyclization and oligomerization. This phenomenon did not adversely impact the ability to form photocrosslinked networks. The copolymer poly (CPP:SA); 80:20 was synthesized as previously described (Rosen et al., *Biomaterials*, 4, 131, 1983; Domb and Langer, *J. Polym. Sci.*, 23, 3375, 1987) and was sieved to less than 100 microns in particle size.

Preparation of Polyanhydride Composite Wafers for Subcutaneous Implantation

Photo-cured wafers. The two methacrylated anhydride monomers, CPP-Me$_2$ and SA-Me$_2$ were combined with the linear copolymer poly (CPP:SA); 80:20 at a weight ratio of 25/25/50, respectively. Photoinitiator, Irgacure 651 (Clba-Geigy) was added at 0.1% (w/w) and mixed to obtain a moldable putty. This was possible due to the waxy nature of the SA-Me$_2$. To form individual wafers, approximately 70 mg of the putty described was placed in a Teflon mold (ID.=8.0 mm) and compressed by hand pressure to obtain soft wafers of 1.0 mm thickness. These wafers were then irradiated on both sides with three 20 second doses of UV light using an Ultracure 100SS photocuring system (EFOS Mississauga, Ontario). A light intensity of 100 mWatt/cm$^2$ was used to cure the material into hard wafers.

Linear polyanhydride wafers. Poly (CPP:SA) (80:20) polymer was compressed in a hardened steal mold using a laboratory Carver press to yield hard disks with identical dimensions (i.e. 8.0 mm dia×1.0 mm).

Sterilization. All polymer wafers were subsequently sterilized by exposure to UV light in a laminar flow hood overnight.

Animal implantation studies. Four rats were weighed and then anesthetized by an intramuscular injection of Ketamine/Xylazine (55/5 mg per Kg). After waiting for the anesthesia to take effect (about five min.), the back of the rat was shaved and sterilized using Betadine.® A dorsal midline incision 2–3 cm in length was made through the skin, layer and two opposing subcutaneous pockets were made in the superficial fascia on either side of the midline incision using blunt dissection techniques. A linear polymer wafer was placed in the left pocket and the photo-cured wafer was placed in the right pocket. The incision was then closed using 3-0 nylon sutures (Ethicon) and the surgical site was swabbed with Betadine® solution to prevent infection. The rats were then allowed to awaken in a warm climate and were checked for any abnormalities in mobility and behavior.n The rats were then individually caged for the duration of the study in accordance with standard procedures.

Retrieval surgeries were done on pairs of rates after 3 weeks and 6 weeks. The rats were euthanized using CO$_2$ asphyxiation. The implants were then excised and surrounding tissue harvested using incisions similar to the ones made previously. Immediately after harvest, the implant and the surrounding tissue was fixed in neutral buffered formalin.

Tissue embedding, sectioning, and staining. After overnight fixation, the implants and surrounding tissues were dehydrated through a series of graded ethanol/xylene solutions, embedded in paraffin, and sectioned to a thickness of 5 μm on a rotary microtome. The sections were mounted onto glass slides, deparaffinized, and stained with hematoxylin and eosin for light microscopic evaluation using standard histological procedures.

RESULTS

3-Week Implants. No necrosis of surrounding tissue or abscess formation was observed upon gross examination of the implantation site prior to implant retrieval. Both of the implants were well tolerated by the surrounding subcutaneous tissue. All of the polymer implants were completely intact and had maintained their overall shape and integrity. The inflammatory and fibrotic response to the photo-cured polymer wafers were significantly less as compared to the linear poly (CPP:SA) wafers. Fibrous capsules surrounding the linear poly (CPP:SA) implants were significant, which in contrast, were negligible around the photo-cured implants. Furthermore, infiltration and integration of the photo-cured polymer with surrounding tissue was significantly greater as compared to the linear polymer. In addition, a greater number of blood vessels was observed around the photo-cured implant. Finally, the cross-linked polymer wafers had undergone degradation and reduced to a thickness of 0.80–0.85 mm (10–16% reduction) while the CPP:SA (80:20) linear polymer wafers were practically unchanged at 0.90–0.95 mm thickness.

6 Week Implants. At six weeks, quite significant differences in tissue reaction to the two implants were observed. Both the polymer implants were intact and had maintained their overall shape and integrity. The photo-cured polymer wafer-implants had undergone significant reductions in thickness to 0.80–0.85 mm (30–37%). In contrast, the linear polymer wafer-implant was essentially unchanged in thickness at 0.90–0.95 mm. Furthermore, the photo-cured implant was very well integrated with the surrounding tissue. In comparison with the linear polymer implant which was still surrounded by a fibrous tissue capsule. In addition, histological examination revealed that vascularity around the photo-cured polymer implant was significantly higher in comparison to the linear poly (CPP:SA) (80:20) implant. After 6 weeks, the fibrous capsules around the linear implants were substantially thicker than at 3 weeks, while the photo-cured semi-IPNs were surrounded only by loose vascularized connective tissue.

7 Week Implants The crosslinked wafer was reduced by more than 60% in diameter while retaining its shape. The linear polyanhydride wafer was virtually unchanged. In addition, excellent tissue integration with vascularity was observed around the crosslinked material, while the tissue reaction to the linear polyanhydride was similar to what was observed at three and six weeks.

CONCLUSION

The overall tissue compatibility, as determined by the extent of tissue integration, neovascularization, and fibrotic response of the photo-cured polymer system, is superior to that of the linear poly (CPP:SA) (80:20). The apparent lack of inflammation indicates that the degradation products of the photo-cured polymer system are well tolerated by the immediate tissue. The rather fast eroding polymer front, as is the case in the photo-cured polymer wafer, has a positive effect on the overall tissue response at that interface. This could prove vital in the ossification of the material when placed in a bone defect to facilitate repair.

EXAMPLE 2

Methods for Evaluating the Compositions

The compositions can be evaluated for strength and modulus by compressive testing, for example, using ASTM standard F451-76 for acrylic bone cement (6 mm round×12 mm length specimens). Uniaxial compression tests can be conducted, for example, at a strain rate of 0.01/sec between two lubricated plates. Automated data acquisition techniques can be used to obtain a computer generated x-y plot of stress versus strain from which compressive strength and modulus at 10% strain can be computed.

Compressive modulus and strengths can be determined on circular waters and cylinders having at least a 2:1 aspect ratio.

The biodegradation of the compositions can be evaluated in vitro by immersing the compositions in various liquids, for example, aqueous solutions at physiological pH, acidic pH, and/or basic pH.

Modifications and variations will be obvious to those skilled in the art from the foregoing detailed description. Such modifications and variations are intended to come within the scope of the appended claims.

We claim:

1. A composition which forms a semi-interpenetrating polymer network following exposure to active species comprising
   a) a linear polymer selected from the group consisting of linear, hydrophobic biodegradable polymers and linear non-degradable hydrophilic polymers; and
   b) at least one monomer or macromer containing at least one free radical polymerizable group, wherein at least one of the monomers or macromers includes an anhydride linkage and a polymerizable group selected from the group consisting of acrylate or methacrylate.

2. The composition of claim 1 in a form suitable for repair or replacement of bone.

3. The composition of claim 1, wherein the biodegradable polymer is formed from one or more monomeric units selected from the group consisting of polyanhydrides, polyorthoesters, polyhydroxy acids, polydioxanones, polycarbonates, and polyaminocarbonates.

4. The composition of claim 1, wherein the biodegradable polymer is formed from one or more monomeric units selected from the group consisting of polyhydroxy acids and polyanhydrides.

5. The composition of claim 1, wherein the monomer or macromer is a methacrylate.

6. The composition of claim 1, wherein the monomer or macromer is polymerized, whereby the composition is in the form of a semi-interpenetrating network.

7. The composition of claim 1, further comprising an excipient selected from the group consisting of hydroxyapatite, plaster of paris, calcium carbonate, tricalcium phosphate, polyphosphates, polyphosphonates and polyphosphites.

8. The composition of claim 1 wherein the covalently crosslinkable monomer or macromer is present in a weight percentage of between 30 and 70 percent by weight.

9. The composition of claim 1 wherein the linear polymer is present in a weight percentage of between 10 and 90 percent by weight.

10. The composition of claim 1, further comprising one or more diagnostic or therapeutic agents.

11. The composition of claim 10, wherein the diagnostic or therapeutic agents are incorporated into a microparticle.

12. The composition of claim 1, further comprising one or more porosity forming agents selected from the group consisting of inorganic salts and proteinaceous materials.

13. A method for repairing or regenerating bone or creating solid prosthetic articles in situ comprising:
   a) injecting into a patient a composition comprising
      i) a linear polymer selected from the group consisting of linear hydrophobic biodegradable polymers and linear non-degradable hydrophilic polymers;
      ii) at least one monomer or macromer containing at least one free radical polymerizable group, wherein at least one of the monomers or macromers includes an anhydride linkage;
   b) forming a semi-interpenetrating network upon exposure to active species.

14. The method of claim 13 wherein the polymer is formed from one or more monomeric units selected from the group consisting of polyanhydrides, polyorthoesters, polyhydroxy acids, polydioxanones, polycarbonates, and polyaminocarbonates.

15. The method of claim 13 wherein the polymer is formed from one or more monomeric units selected from the group consisting of polyhydroxy acids and polyanhydrides.

16. The method of claim 13 wherein the monomer or macromer is a (meth)acrylate.

17. The method of claim 13 wherein the composition further comprises an excipient selected from the group consisting of hydroxyapatite, plaster of paris, calcium carbonate, tricalcium phosphate, polyphosphates, polyphosphonates and polyphosphites.

18. The method of claim 13 wherein the covalently crosslinkable monomer or macromer is present in a weight percentage of between 30 and 70 percent by weight.

19. The method of claim 13 wherein the linear polymer is present in a weight percentage of between 10 and 90 percent by weight.

20. The method of claim 13 wherein the composition further comprises one or more diagnostic or therapeutic agents.

21. The method of claim 20 wherein the diagnostic or therapeutic agents are incorporated into a microparticle.

22. The method of claim 13 wherein the composition further comprises one or more porosity forming agents selected from the group consisting inorganic salts and proteinaceous materials.

23. A method for preparing solid articles for use in repairing or regenerating bone comprising
    a) casting or injecting into a suitable mold a composition comprising
        i) a linear polymer selected from the group consisting of linear hydrophobic biodegradable polymers and linear non-degradable hydrophilic polymers;
        ii) at least one monomer or macromer containing at least one free radical polymerizable group, wherein at least one of the monomers or macromers includes an anhydride linkage;
    b) forming a semi-interpenetrating network upon exposure to active species.

24. The method of claim 23 wherein the polymer is formed from one or more monomeric units selected from the group consisting of polyanhydrides, polyorthoesters, polyhydroxy acids, polydioxanones, polycarbonates, and polyaminocarbonates.

25. The method of claim 23 wherein the polymer is formed from one or more monomeric units selected from the group consisting of polyhydroxy acids and polyanhydrides.

26. The method of claim 23 wherein the monomer or macromer is a (meth)acrylate.

27. The method of claim 23 wherein the composition further comprises an excipient selected from the group consisting of hydroxyapatite, plaster of paris, calcium carbonate, tricalcium phosphate, polyphosphates, polyphosphonates and polyphosphites.

28. The method of claim 23 wherein the covalently crosslinkable monomer or macromer is present in a weight percentage of between 30 and 70 percent by weight.

29. The method of claim 23 wherein the linear polymer is present in a weight percentage of between 10 and 90 percent by weight.

30. The method of claim 23 wherein the composition further comprises one or more diagnostic or therapeutic agents.

31. The method of claim 30 wherein the diagnostic or therapeutic agents are incorporated into a microparticle.

32. The method of claim 23 wherein the composition further comprises one or more porosity forming agents selected from the group consisting inorganic salts and proteinaceous materials.

* * * * *